(12) United States Patent
Yokota (10) Patent No.: US 8,079,951 B2
(45) Date of Patent: Dec. 20, 2011

(54) INTUBATION ASSISTANCE APPARATUS

(75) Inventor: Hidetaka Yokota, Tokyo (JP)

(73) Assignee: Hoya Corporation, Tokyo (JP)

( * ) Notice: Subject to any disclaimer, the term of this patent is extended or adjusted under 35 U.S.C. 154(b) by 1169 days.

(21) Appl. No.: 11/552,262

(22) Filed: Oct. 24, 2006

(65) Prior Publication Data

US 2007/0106117 A1    May 10, 2007

(30) Foreign Application Priority Data

Oct. 24, 2005  (JP) ................. P2005-309153

(51) Int. Cl.
*A61B 1/267* (2006.01)
*A61B 1/04* (2006.01)

(52) U.S. Cl. ............... 600/120; 600/131; 600/188

(58) Field of Classification Search ............ 600/109, 600/114, 117, 120, 160, 184, 185, 188, 190, 600/194, 131
See application file for complete search history.

(56) References Cited

U.S. PATENT DOCUMENTS

| | | | |
|---|---|---|---|
| 4,086,919 A | 5/1978 | Bullard | |
| 4,592,343 A | 6/1986 | Upsher | |
| 4,660,982 A * | 4/1987 | Okada | 356/636 |
| 4,742,819 A | 5/1988 | George | |
| 5,063,907 A | 11/1991 | Musicant et al. | |
| 5,174,104 A | 12/1992 | Wehler et al. | |
| 5,263,472 A | 11/1993 | Ough | |
| 5,287,848 A | 2/1994 | Cubb et al. | |
| 5,363,838 A | 11/1994 | George | |
| 5,515,160 A * | 5/1996 | Schulz et al. | 356/241.1 |
| 5,800,344 A * | 9/1998 | Wood et al. | 600/188 |
| D399,957 S | 10/1998 | Chernov et al. | |
| 5,827,178 A | 10/1998 | Berall | |
| 6,494,828 B1 | 12/2002 | Berall | |
| 6,554,765 B1 * | 4/2003 | Yarush et al. | 600/132 |
| 6,655,377 B2 * | 12/2003 | Pacey | 128/200.26 |
| 6,843,769 B1 | 1/2005 | Gandarias | |
| D533,939 S * | 12/2006 | Root et al. | D24/138 |
| 7,156,091 B2 | 1/2007 | Koyama et al. | |
| 7,182,728 B2 | 2/2007 | Cubb et al. | |

(Continued)

FOREIGN PATENT DOCUMENTS

EP     0499784     8/1992

(Continued)

OTHER PUBLICATIONS

English language Abstract of EP 0499784, Aug. 26, 1992.

(Continued)

*Primary Examiner* — John P Leubecker (74) *Attorney, Agent, or Firm* — Greenblum & Bernstein, P.L.C.

(57) ABSTRACT

An intubation assistance apparatus includes a main body having a proximal end portion; an intubation assistance instrument having an elongated insertion section for insertion into a target site or its vicinity of a patient from a mouth cavity of the patient, the inserting section being formed with a tube guide for leading the intubation tube toward the observation site; and an imaging device for taking an image of an observation site at a distal end portion of the insertion section as an electronic image. The main body includes a display having a screen for displaying the electronic image taken by the imaging device, and the screen of the display is adapted to indicate a target mark for adjusting or setting an advancing direction of the intubation tube to the observation site displayed on the screen in the electronic image displayed on the screen.

20 Claims, 8 Drawing Sheets

U.S. PATENT DOCUMENTS

| | | | |
|---|---|---|---|
| 2002/0022769 A1 | | 2/2002 | Smith et al. |
| 2003/0195390 A1* | | 10/2003 | Graumann .................... 600/188 |
| 2005/0150500 A1* | | 7/2005 | Koyama et al. .......... 128/207.14 |
| 2005/0261550 A1 | | 11/2005 | Akimoto et al. |
| 2006/0004258 A1* | | 1/2006 | Sun et al. ....................... 600/160 |
| 2006/0065268 A1 | | 3/2006 | Koyama et al. |

FOREIGN PATENT DOCUMENTS

| | | |
|---|---|---|
| EP | 1640033 | 3/2006 |
| JP | 2000-175867 | 6/2000 |
| JP | 2002-509768 | 4/2002 |
| JP | 2004-313271 | 11/2004 |
| JP | 3108837 | 3/2005 |
| JP | 2005-143756 | 6/2005 |
| JP | 2005-211535 | 8/2005 |
| WO | WO 9949910 A2 * | 10/1999 |
| WO | 02/11608 | 2/2002 |

OTHER PUBLICATIONS

"TUBE 'EM in the streets," by Terry Abrams, MSC, EMT-P, Journal of Emergency Medical Services, vol. 20, No. 4, pp. 30-40, Apr. 1995.
"Teaching Tips for Successful Tubes," by Terry Abrams, MSC, EMT-P, Journal of Emergency Medical Services, vol. 20, No. 4, p. 41, Apr. 1995.
"Rapid Sequence Intubation Don't Fight it," by Mike Hartley, REMT-P, Journal of Emergency Medical Services, vol. 20, No. 4, pp. 42-44, Apr. 1995.
English Language Abstract of JP 2000-175867.
U.S. Appl. No. 11/552,235 to Yokota et al., filed Oct. 24, 2006.
U.S. Appl. No. 11/552,184 to Yokota, filed Oct. 24, 2006.
Internet press release dated Jul. 6, 2006 for the PENTAX AWS-S100 and the PENTAX PBLADE: ITL-S downloaded from the internet at: http://www.pentax.co.jp/english/news/2006/200633.html.
A product description dated Jul. 6, 2006, downloaded from the internet at: www.pentaxmedical.com/osc/catalog/product_info.php/cPath/44_26/products_id/36).
Internet Japanese article dated Jul. 7, 2006, downloaded from the internet website "Tech-On!" at: http://techon.nikkeibp.co.jp/article/NEWS/20060707/118959/, along with an English-language translation thereof.
Internet Japanese blog entry dated Jul. 6, 2006, downloaded from the internet website "Endoscopin" at: http://endoscopin.blog40.fc2.com/page-1.html, along with an English-language translation thereof.
Internet Japanese article dated Jul. 10, 2006; downloaded from the internet website "Design News Japan" at: http://www.design-newsjapan.com/news/200607/10med_pentax060707.html, along with an English-language translation thereof.

* cited by examiner

INTUBATION ASSISTANCE APPARATUS

BACKGROUND OF THE INVENTION

1. Field of the Invention

The present invention relates to an intubation assistance apparatus for use in inserting a distal end of an intubation tube to be connected to a respirator into a target site such as a trachea of a patient.

2. Description of the Prior Art

It is sometimes necessary to practice artificial respiration, as a first-aid lifesaving treatment for a patient who is suffering from unconsciousness caused by an accident or the like. Although the artificial respiration may be practiced without having to use any instrument or apparatus, it is often the case that a respirator is used for that purpose.

In the event that a respirator is utilized to conduct artificial respiration, an intubation tube whose proximal end is connected to the respirator is inserted into the trachea of a patient to supply air to the trachea from the respirator via the tube.

In the meantime, if a patient loses consciousness, the root of a tongue is retracted to thereby block up a respiratory tract (air passage) because of the relaxation of muscles of the pharynx and the larynx and/or the gravity-caused loosening of a lower jaw.

Therefore, in the case where the afore-mentioned intubation tube is to be inserted into the trachea or a target site, it is essential to first open the blocked respiratory tract and secure an air passage by pulling up the tongue.

As an instrument for use in securing the air passage, there is known an intubation assistance instrument which is called an oral airway (see, e.g., US-A 2005-0150500).

Such an intubation assistance instrument includes an insertion section to be inserted into the trachea or its vicinity of a patient, and a guide portion (guide groove) provided in the insertion section for leading an intubation tube to the trachea of the patient when the intubation tube is inserted into the trachea of the patient. The intubation assistance instrument is inserted through the mouth of a patient who has lost consciousness, and an appropriate portion on the side of the distal end comes into contact with and lifts up a tongue root portion of the patient, thus securing the air passage.

As described in the above-mentioned prior art, the oral airway (intubation assistance instrument) is normally used in a state that the proximal end of the intubation assistance instrument is coupled to a main body of an intubation assistance apparatus (hereinafter, this state will be referred to as "coupling state"). The intubation assistance apparatus includes an image taking means (image pick-up device) for taking an image of an observation site at a distal end portion of the intubation assistance instrument as an electronic image, and a display for displaying the electronic image taken by the image taking means.

Further, in the intubation assistance apparatus of the above-mentioned prior art, there is formed an internal bore in which an image guide is inserted. The internal bore is formed so as to be substantially parallel with the guide groove.

Figure 1:
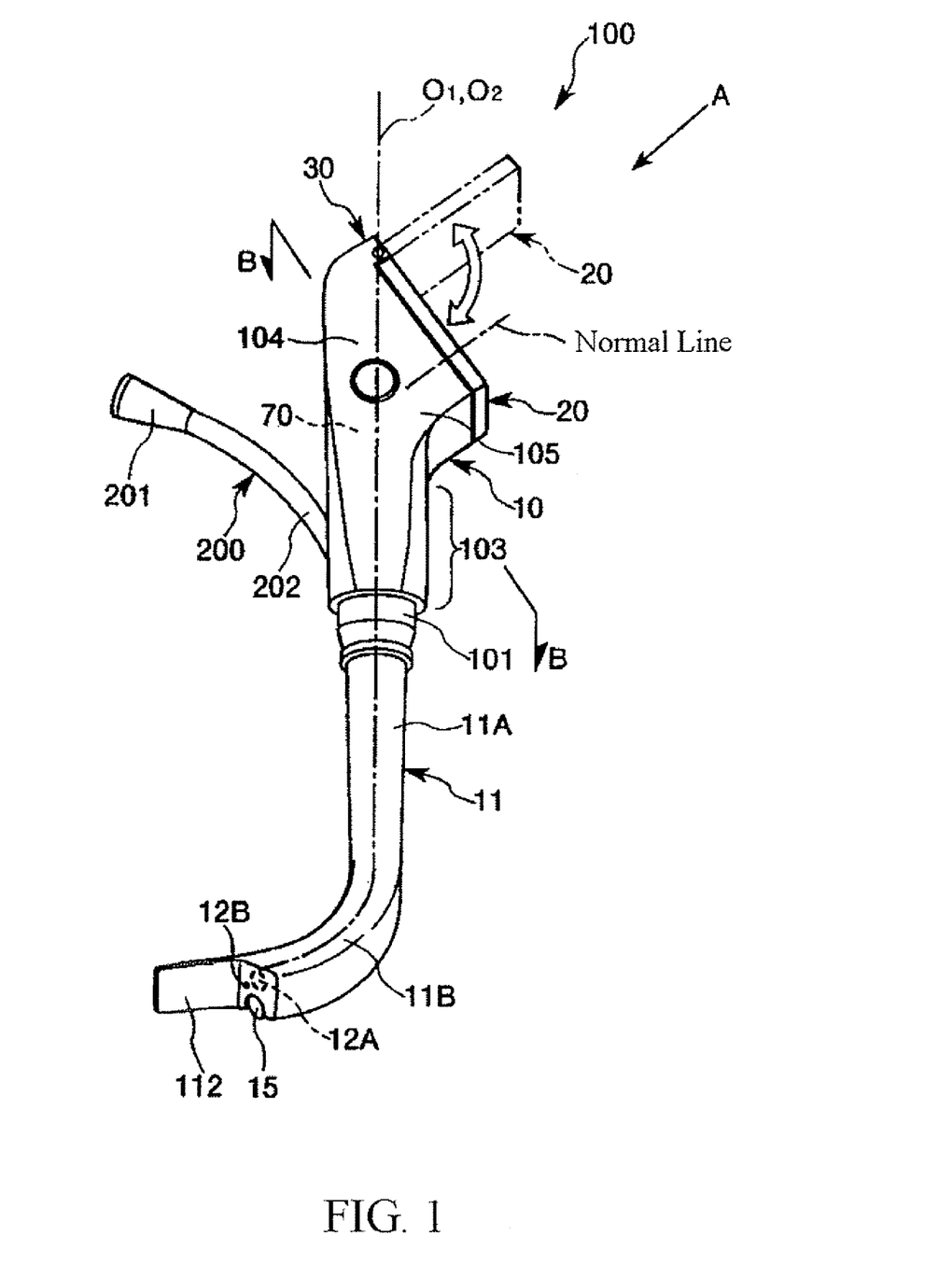
FIG. 1 is a perspective view which shows an intubation assistance apparatus according to the present invention.

When the intubation assistance apparatus is used in a state shown in FIG. 1 of the above-mentioned prior art, that is, when the apparatus is used in a state that the center of the screen of the display is aligned with the center of the entrance of the trachea of a patient displayed on the screen, the intubation tube is advanced toward a direction dislocated from the entrance of the trachea of the patient when the intubation is pushed forward from the distal end portion of the insertion section of the intubation assistance instrument.

Since there is a problem as described above, that is, the intubation tube is advanced toward a direction dislocated from the entrance of the trachea of the patient, the operator has to operate the intubation assistance instrument so that the intubation tube is correctly advanced toward the entrance of the trachea of the patient. This results in a problem in that the manipulability of the intubation assistance apparatus when the intubation tube is inserted into a target site of a patient is lowered.

SUMMARY OF THE INVENTION

It is therefore an object of the present invention to provide an intubation assistance apparatus having superior manipulability when an intubation tube is inserted into a target site of a patient.

In order to achieve this object, the present invention is directed to an intubation assistance apparatus which includes a main body having a proximal end portion; an intubation assistance instrument having an elongated insertion section for insertion into a target site or its vicinity of a patient from the mouth of the patient, the inserting section being formed with guide means for leading an intubation tube toward the target site when the intubation tube is to be inserted into the target site of the patient; and image taking means for taking an image of an observation site at a distal end portion of the insertion section as an electronic image. The main body includes a display having a screen for displaying the electronic image taken by the image taking means, and the screen of the display is adapted to indicate a target mark for adjusting or setting an advancing direction of the intubation tube to the observation site displayed on the screen in the electronic image displayed on the screen.

According to the intubation assistance apparatus of the present invention described above, it is possible to intubate an intubation tube into the target site of a patient reliably and in a short time. That is, it is possible to provide an intubation assistance apparatus having superior manipulability in inserting an intubation tube into the target site of the patient.

In the intubation assistance apparatus according to the present invention described above, it is preferred that the intubation assistance apparatus is configured so that the intubation tube is advanced toward the observation site in the electronic image displayed on the screen when the intubation tube is pushed out from the distal end of the insertion section with a state that the target mark is set to the observation site displayed on the screen.

This also makes it possible to intubate an intubation tube into the target site of a patient more reliably and in a shorter time. That is, the intubation assistance apparatus can have more superior manipulability in inserting the intubation tube into the target site of the patient.

Further, in the intubation assistance apparatus according to the present invention described above, it is also preferred that the intubation assistance instrument having a distal end portion having a central axis, and the central axis of the distal end portion of the intubation assistance instrument is substantially in parallel with the central axis of the intubation tube inserted into the guide means, and wherein a central axis of the field of view of the image taking means is located on the opposite side of the central axis of the intubation tube inserted into the guide means with respect to the central axis of the distal end portion of the intubation assistance instrument, and further the central axis of the field of view of the image taking means is inclined with respect to the central axis of the distal end portion of the intubation assistance instrument so that the central axis of the field of view of the image taking means is directed toward the intubation tube inserted into the guide means.

This also makes it possible to intubate an intubation tube into the target site of a patient more reliably and in a shorter time. That is, the intubation assistance apparatus can have more superior manipulability in inserting the intubation tube into the target site of the patient.

Furthermore, in the intubation assistance apparatus according to the present invention described above, it is also preferred that the observation site is positioned on the extended line of the central axis of the intubation tube held by the guide means in a state that the target mark is set to an image of the observation site displayed on the screen.

This also makes it possible to intubate an intubation tube into the target site of a patient more reliably and in a shorter time. That is, the intubation assistance apparatus can have more superior manipulability in inserting the intubation tube into the target site of the patient.

Furthermore, in the intubation assistance apparatus according to the present invention described above, it is also preferred that the target mark is indicated at a position in which the center of the target mark is eccentric to the center of the screen.

This makes it possible to improve manipulability of the intubation assistance apparatus in inserting the intubation tube into the target site of the patient.

Furthermore, in the intubation assistance apparatus according to the present invention described above, it is also preferred that the color of the target mark is any color other than red.

This makes it possible to improve visibility of the target mark during the use of the intubation assistance apparatus.

Furthermore, in the intubation assistance apparatus according to the present invention described above, it is also preferred that the color of the target mark is green.

This also makes it possible to improve visibility of the target mark during the use of the intubation assistance apparatus.

Moreover, in the intubation assistance apparatus according to the present invention described above, it is also preferred that the target mark is provided on the screen by printing it on the screen.

By using such a printing method, the target mark can be provided easily.

Moreover, in the intubation assistance apparatus according to the present invention described above, it is also preferred that the display section is rotatable with respect to the main body.

This makes it possible to direct the display to a desired direction despite the direction of the distal end portion of the intubation assistance instrument.

Moreover, in the intubation assistance apparatus according to the present invention described above, it is also preferred that the guide section is configured so that the intubation tube can be removed from the guide means in a state that the insertion section is inserted into the observation site of the patient.

With this structure, only the intubation tube can remain inserted into the mouth of the patient.

Moreover, in the intubation assistance apparatus according to the present invention described above, it is also preferred that the image taking means includes an image pick-up device provided in the main body and leading means provided in the intubation assistance instrument for leading an image of an object to be taken to the image pick-up device.

With this structure, it is possible to take an image of the observation site located in front of the distal end of the intubation assistance instrument as an electronic images and thus obtained image can be displayed on the screen for observation.

These and other objects, structures and results of the present invention will be apparent more clearly when the following detailed description of the preferred embodiments is considered taken in conjunction with the appended drawings.

DETAILED DESCRIPTION OF THE PREFERRED EMBODIMENTS

Hereinbelow, a preferred embodiment of an intubation assistance apparatus according to the present invention will be described in detail with reference to the accompanying drawings.

Figure 2:
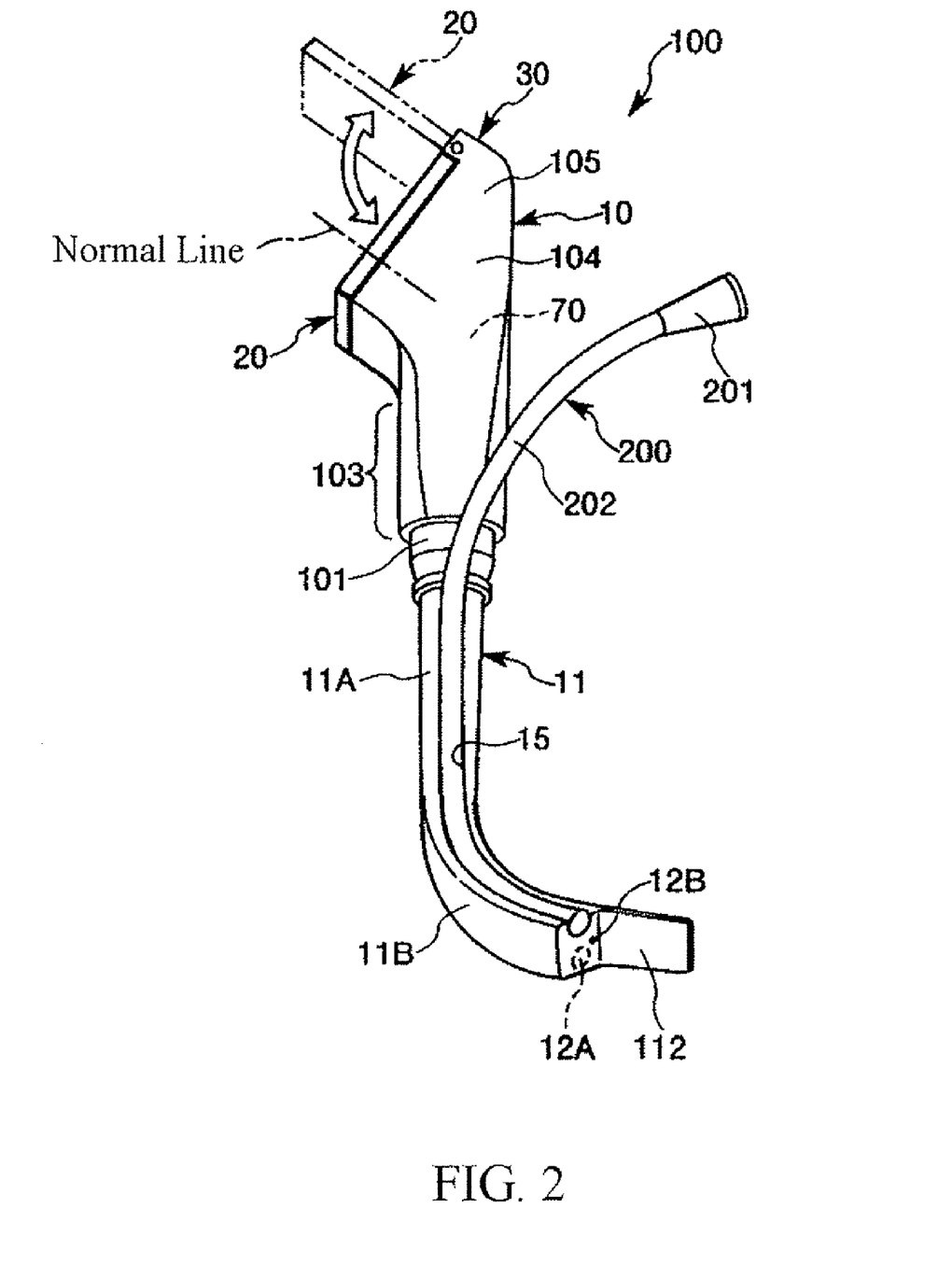
FIG. 2 is another perspective view which shows the intubation assistance apparatus according to the present invention.
Figure 3:
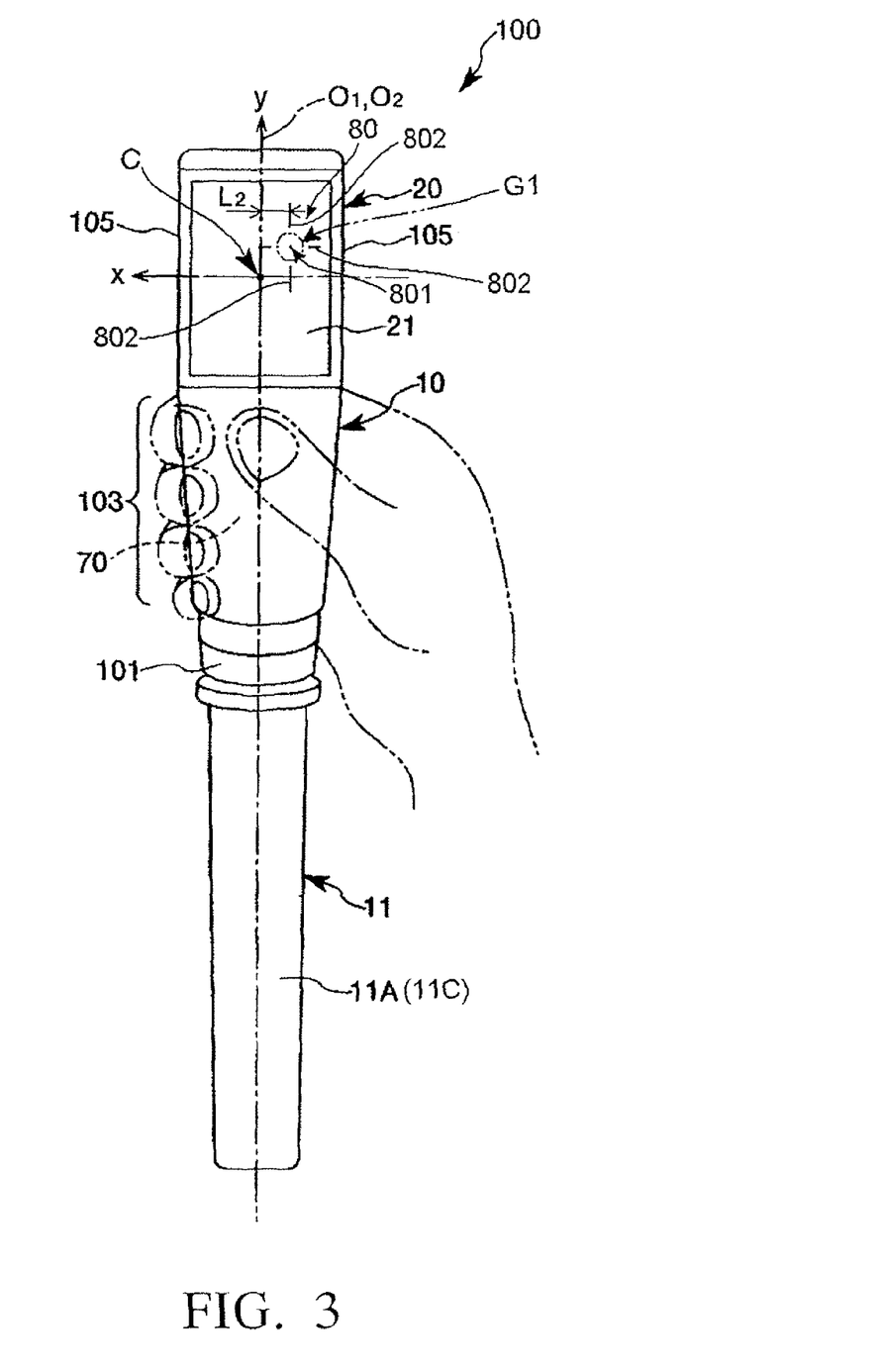
FIG. 3 is an illustration which shows the intubation assistance apparatus shown in FIG. 1 viewed from the direction indicated by the arrow A in FIG. 1.
Figure 4:
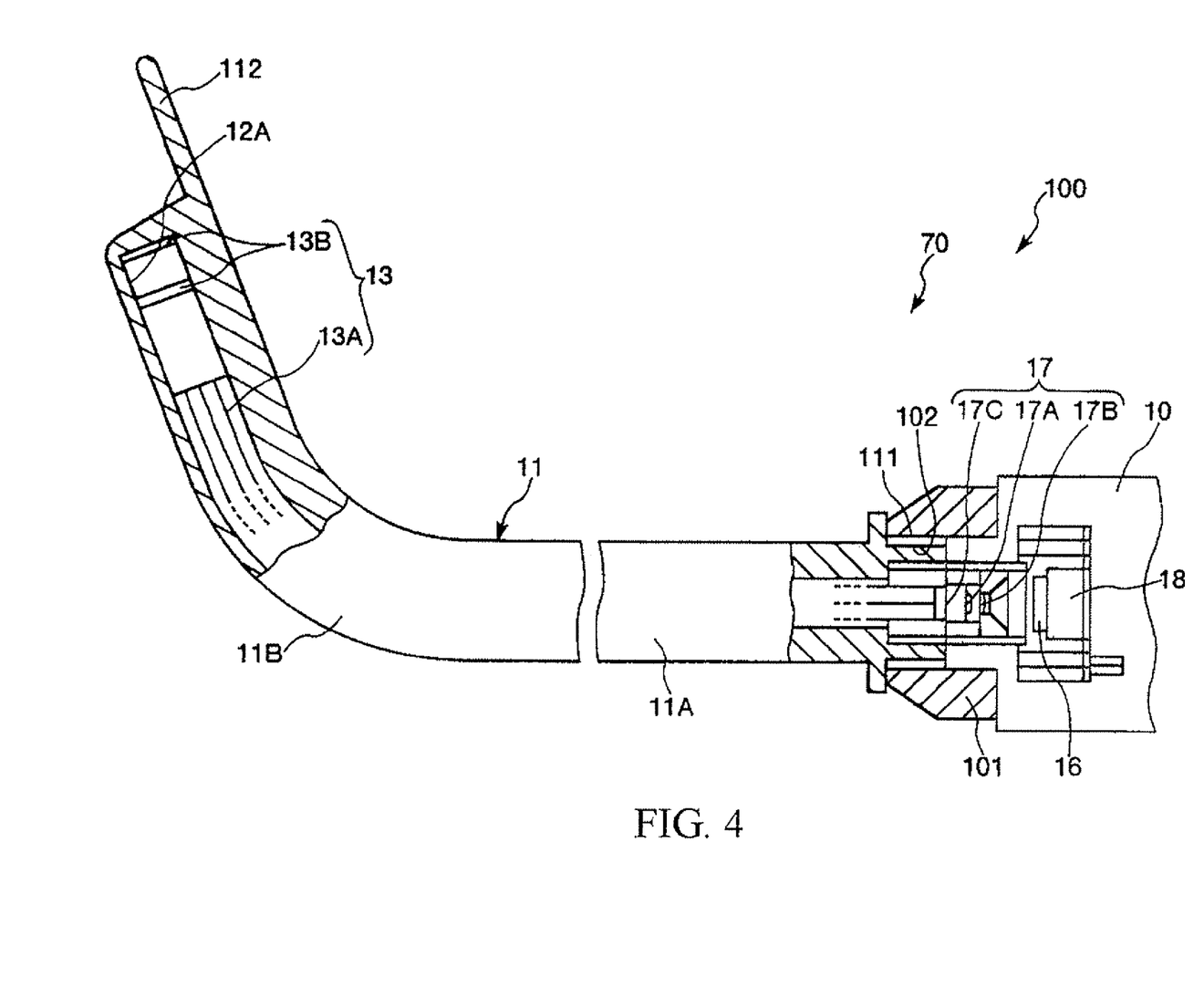
FIG. 4 is a cross-sectional view taken along line B-B in FIG. 1.
Figure 5:
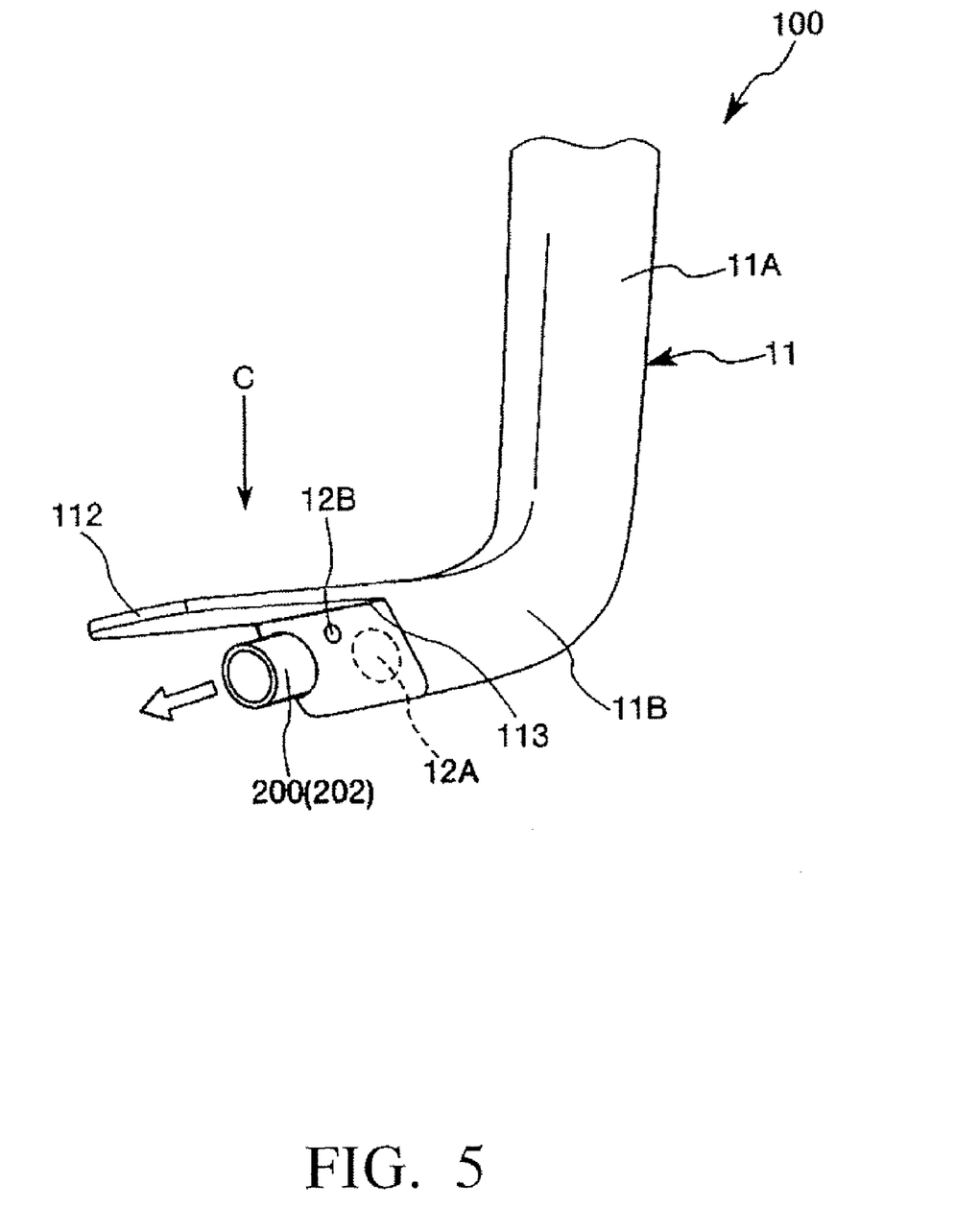
FIG. 5 is a perspective view which shows a state that an intubation tube is pushed out from a distal end of an intubation assistance instrument of the intubation assistance apparatus shown in FIGS. 1 and 2.
Figure 6:
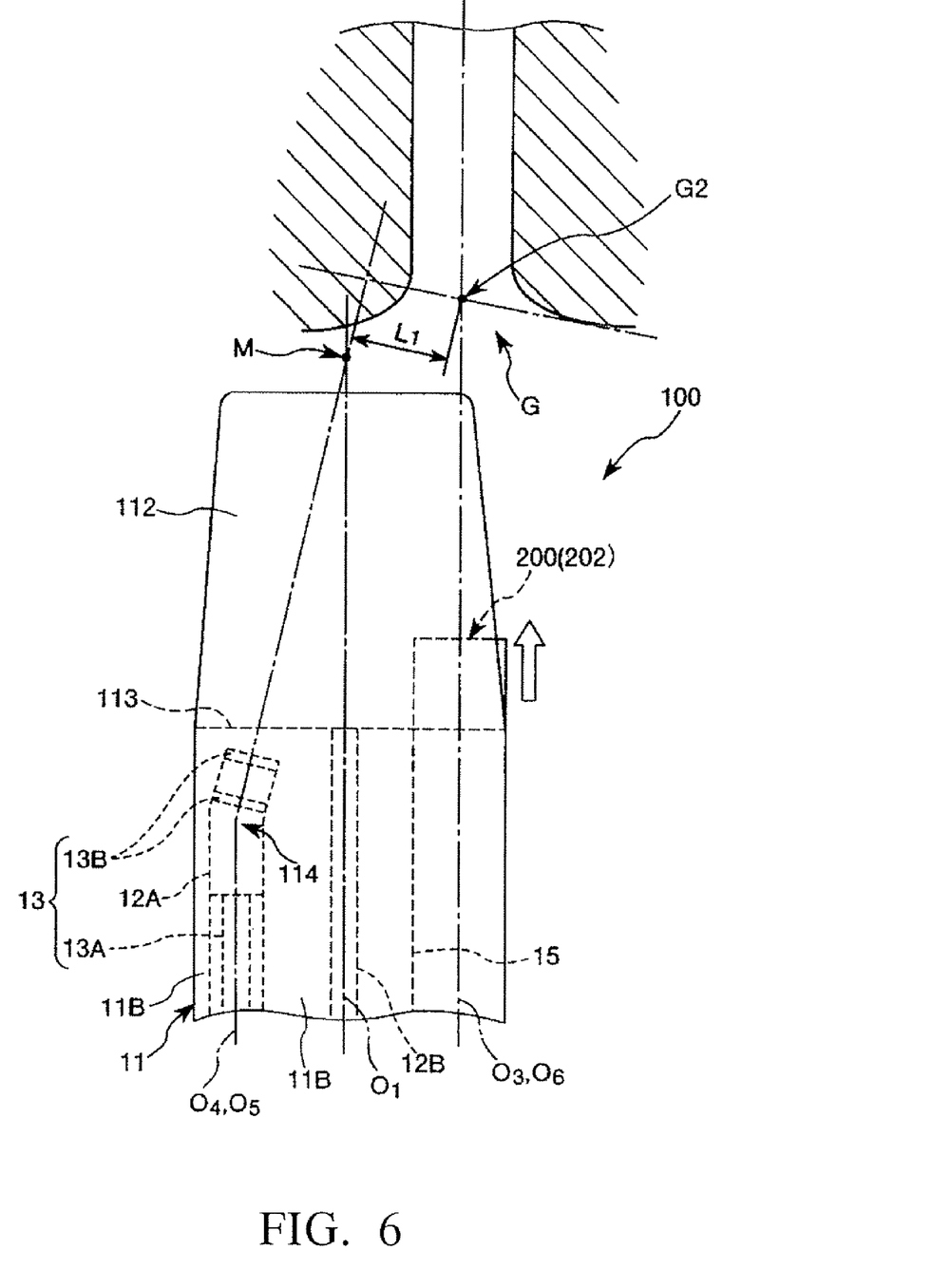
FIG. 6 is an illustration which shows the distal end portion of the intubation assistance instrument shown in FIG. 5 viewed from the direction indicated by the arrow C.
Figure 7:
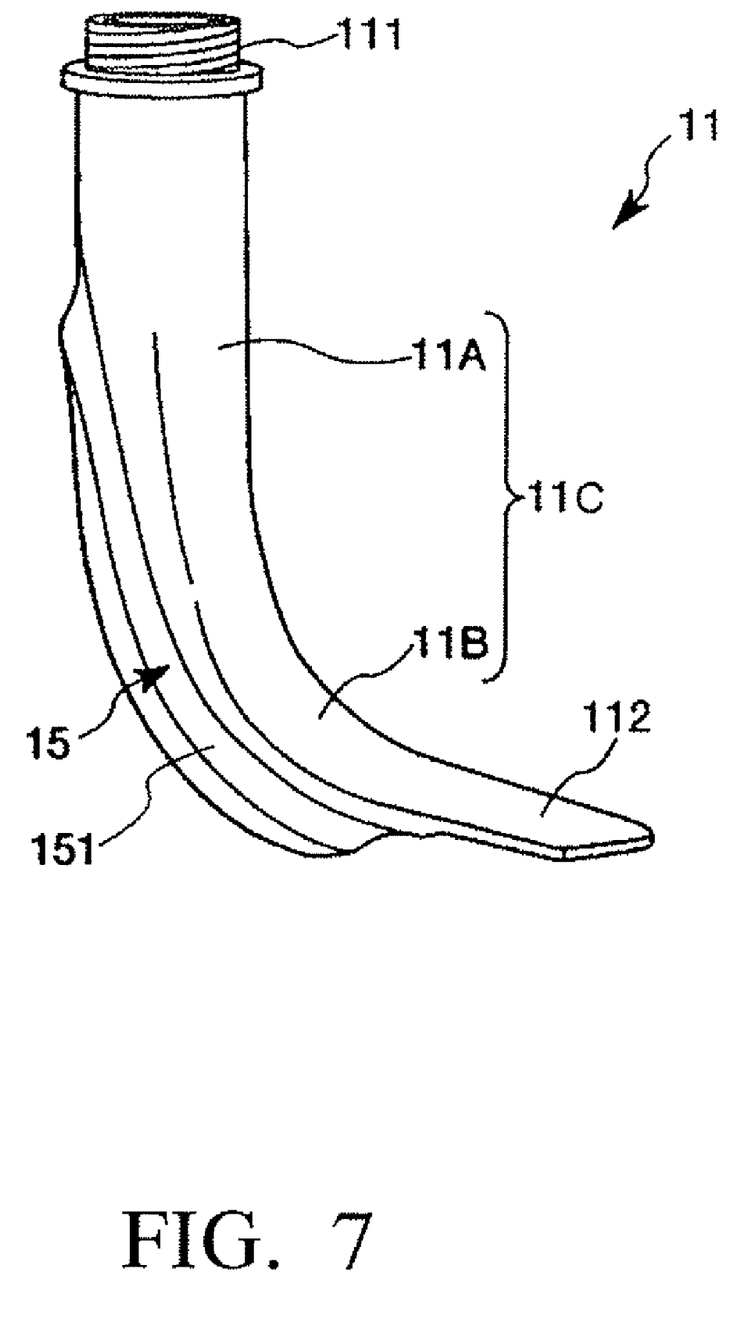
FIG. 7 is a perspective view which shows an intubation assistance instrument of the intubation assistance apparatus shown in FIGS. 1 and 2.
Figure 8:
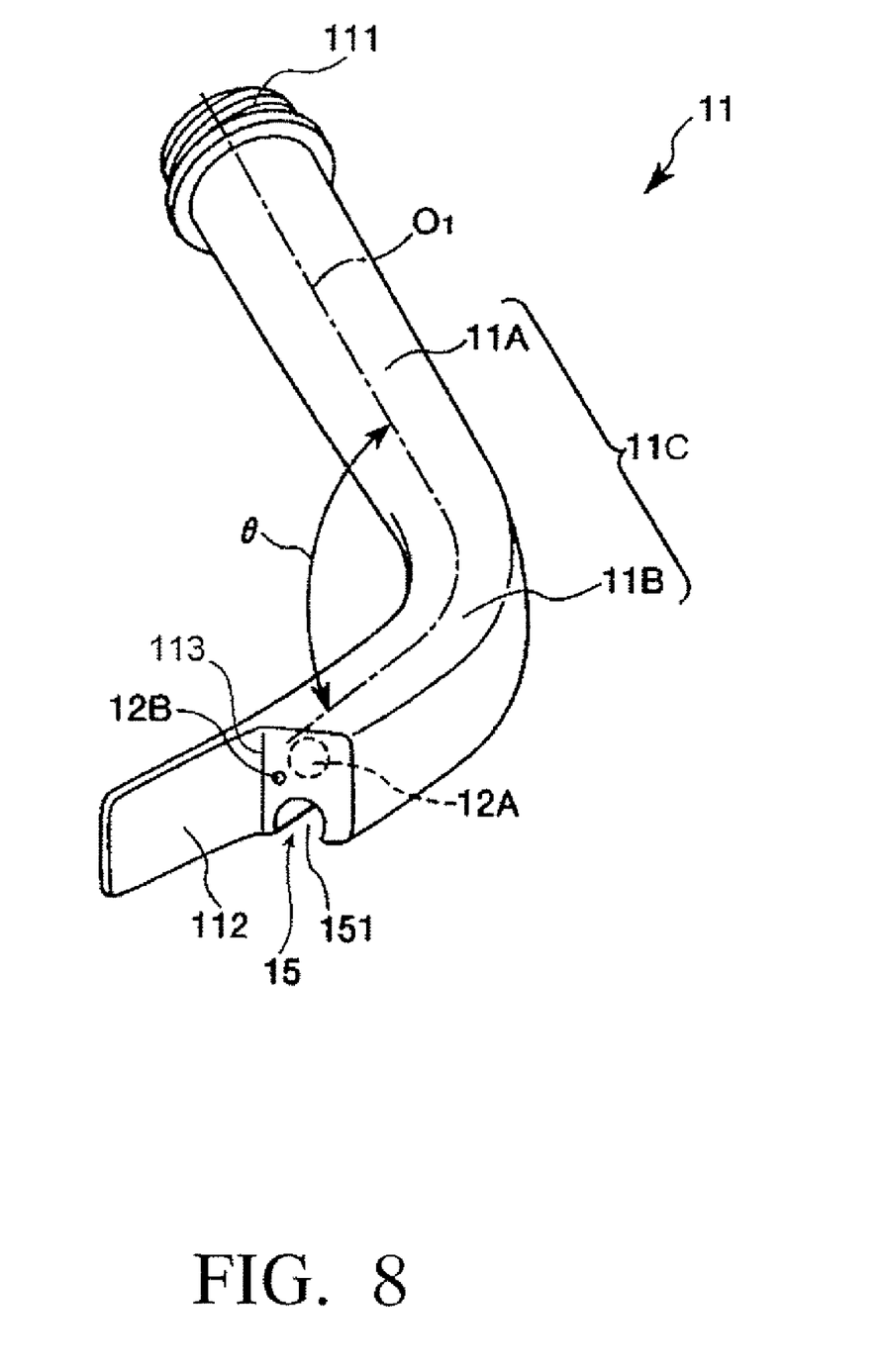
FIG. 8 is another perspective view which shows the intubation assistance instrument of the intubation assistance apparatus shown in FIGS. 1 and 2.

FIG. 1 is a perspective view which shows an intubation assistance apparatus according to the present invention; FIG. 2 is another perspective view which shows the intubation assistance apparatus according to the present invention; FIG. 3 is an illustration which shows the intubation assistance apparatus shown in FIG. 1 viewed from the direction indicated by the arrow A in FIG. 1; FIG. 4 is a cross-sectional view taken along line B-B in FIG. 1; FIG. 5 is a perspective view which shows a state that an intubation tube is pushed out from a distal end of an intubation assistance instrument of the intubation assistance apparatus shown in FIGS. 1 and 2; FIG. 6 is an illustration which shows the distal end portion of the intubation assistance instrument shown in FIG. 5 viewed from the direction indicated by the arrow C; FIG. 7 is a perspective view which shows an intubation assistance instrument of the intubation assistance apparatus shown in FIGS. 1 and 2; and FIG. 8 is another perspective view which shows the intubation assistance instrument of the intubation assistance apparatus shown in FIGS. 1 and 2.

Note that in FIG. 3 an intubation tube is omitted. Further, in FIG. 3, the center of the screen is defined as the origin, a direction extending toward the left side from the origin is defined as an X-axis plus direction, a direction extending toward the right side from the origin is defined as an X-axis minus direction, a direction extending toward the upper side from the origin is defined as a Y-axis plus direction, and a direction extending toward the lower side from the origin is defined as a Y-axis minus direction, respectively. Furthermore, in the following description, the upper side and the lower side in FIGS. 1 to 5 will be referred to as "proximal end" or "proximal end portion" and "distal end" or "distal end portion", respectively, for the purpose of clarity.

The intubation assistance apparatus 100 shown in FIGS. 1 and 2 includes a main body 10, an intubation assistance instrument 11 and an image taking means 70, and the intubation assistance apparatus 100 is used in a state that these components are assembled together.

Further, as shown in FIGS. 1 and 2, the intubation assistance apparatus 100 is used in combination with an intubation tube 200 which is to be inserted into a target site of a patient through the mouth (mouth cavity) thereof. In this regard, please note that the following description of this embodiment will be made based on one exemplary case where the target site of a patient is a trachea of the patient.

Hereinbelow, detailed descriptions will be made with regard to each of these components.

The intubation assistance instrument 11 shown in FIGS. 7 and 8 is formed from an elongated member, and it is used by being inserted into the vicinity of the rima glottidis G of a patient who has lost consciousness from the mouth (mouth cavity) of the patient. An air passage for the patient is secured by bringing an appropriate portion on the side of a distal end of the intubation assistance instrument 11 into contact with the root of a tongue of the patient.

As illustrated in FIGS. 7 and 8, the intubation assistance instrument 11 includes an insertion section 11C, a groove (guide means) 15 formed in the insertion section 11C, and a first internal bore 12A and a second internal bore 12B both formed inside the insertion section 11C.

The insertion section 11C is constituted from a straight portion 11A and a curved portion 11B which is curved and extends from the distal end side of the straight portion 11A continuously. The outer circumferential surface of the straight portion 11A is rounded to form a substantially column-like shape.

Further, the proximal end part of the straight portion 11A is formed with a male thread 111. The male thread 111 is adapted to be threaded with a female thread 102 formed in a coupling member 101 of the main body 10 (see FIG. 4). When the male thread 111 is threaded with the female thread 102, the intubation assistance instrument 11 is mounted to the main body to provide the intubation assistance apparatus 100 in the assembled state.

Further, by disengaging the male thread 111 of the straight portion 11A from the female thread 102 of the main body 10, the intubation assistance instrument 11 is removed from the main body 10. Therefore, by removing the intubation assistance instrument 11 which has been used for a patient from the main body 10, it is possible to attach a new intubation assistance instrument 11 to the main body 10.

As described above, the curved portion 11B extends from the distal end side of the straight portion 11A in a continuous manner. The curved portion 11B is curved so that the distal end thereof is directed to a direction inclined with respect to the straight portion 11A. The inclined angle θ (see FIG. 8) is not particularly limited, but it is preferably in the range of 70 to 140°, and more preferably in the range of 90 to 120°.

In this intubation assistance instrument 11, by constructing the insertion section 11C from the straight portion 11A and the curved portion 11B so that the entire shape thereof forms an L-shape, the intubation assistance instrument 11 can be inserted into the mouth of a patient easily to thereby secure an air passage of the patient reliably.

Further, on the distal end of the curved portion 11B, a plate-shaped protruding portion (tongue piece) 112 is integrally formed. The protruding portion 112 is used for pushing up or lifting up the epiglottis or the root of tongue of the patient when securing the air passage of the patient.

As shown in FIGS. 7 and 8, on the side portion of the intubation assistance instrument 11 (insertion section 11C), the groove (guide means) 15 is formed from the midway of the straight portion 11A to the distal end portion of the curved portion 11B. This groove 15 has a function of guiding or leading an intubation tube 200 which is inserted from the mouth of a patient to the rima glottidis G of the patient when the intubation tube 200 is intubated into the rima glottidis G (trachea) of the patient after the air passage thereof has been secured by the intubation assistance instrument 11.

As shown in FIG. 6, in the region of the curved portion 11B of the intubation assistance instrument 11 (that is, in the distal end portion of the intubation assistance instrument 11) the central axis $O_3$ of the groove 15 is substantially in parallel with the central axis $O_1$ of the intubation assistance instrument 11. Further, as shown in FIG. 8, the distal end of the groove 15 is opened toward the direction of the central axis $O_3$ (that is, toward the protruding direction of the protruding portion 112).

In more details, the intubation tube 200 is inserted into the groove 15 as shown in FIG. 5 after the air passage of the patient has been secured, and then advanced toward the distal end of the intubation assistance instrument 11. At this time, the intubation tube 200 is slidably advanced within the groove 15 with being guided by the inner wall of the groove 15. Then, the distal end of the intubation tube 200 protrudes from the distal end of the intubation assistance instrument 11 and further advanced toward the rima glottidis G of the patient which is located back of larynx thereof (see FIG. 6).

The groove 15 is formed to have a C-shaped cross section. With this structure, the intubation tube 200 can be removed or detached from the groove 15 through an opening (slit) 151 in a state that the insertion section 11C remains inserted into the rima glottidis G of the patient. As a result, only the intubation tube 200 can be left within the mouth cavity of the patient with a state that the intubation tube 200 is inserted into the trachea of the patient.

In this regard, it is to be noted that the cross-section of the groove 15 shown in the drawings has a substantially C-shape, but the cross-sectional shape there of is not limited thereto and it may be formed into a U-shape.

Further, it is preferred that the width (maximum width) of the groove 15 is set to be slightly larger than the outer diameter of the intubation tube 200. With this result, the intubation tube 200 can be smoothly advanced within the groove 15.

As shown in FIG. 4, the first internal bore 12A is formed inside the intubation assistance instrument 11 along the longitudinal direction thereof. The first internal bore 12A is positioned on the opposite side of the groove 15 with respect to the central axis $O_1$ of the intubation assistance instrument 11 (see, for example, FIG. 6). The first internal bore 12A is formed so as to have a substantially circular cross-section.

As shown in FIG. 4, the first internal bore 12A is opened at the proximal end of the intubation assistance instrument 11 (that is, the straight portion 11A), and closed at the distal end of the intubation assistance instrument 11 (that is, the curved portion 11B). In this regard, it is to be noted that a portion of the intubation assistance instrument 11 that closes the distal end of the internal bore 12A is formed to be substantially transparent.

Further, as shown in FIG. 6, the central axis $O_4$ of the first internal bore 12A is in parallel with the central axis $O_1$ of the intubation assistance instrument 11 to a portion 114 of the first internal bore 12A which is in the vicinity of the proximal end of the protruding portion 112 (see the angled point 114 of the central axis $O_4$ in FIG. 6), and the central axis $O_4$ of the first internal bore 12A beyond the angled point 114 is inclined toward the groove 15 with respect to the central axis $O_1$ of the intubation assistance instrument 11. With this structure, the central axis $O_5$ which corresponds to the center of the field of view of the image taking means 70 disposed inside the internal bore 12A is also inclined toward the groove 15 with respect to the central axis $O_1$ of the intubation assistance instrument 11.

Namely, in the assembled state of the intubation assistance apparatus 100, inside the first internal bore 12A, there are disposed a bundle of optical fibers 13A which constitutes a part of the image taking means 70 and an objective lens 13B which is positioned in front of the bundle of optical fibers 13A. The details of the image taking means 70 will be described later.

The second internal bore 12B of which diameter is smaller than the diameter of the first internal bore 12A is also formed inside the intubation assistance instrument 11. The second internal bore 12B is formed in parallel with the central axis $O_1$ of the intubation assistance instrument 11.

Both the ends of the second internal bore 12 are opened at the proximal and distal ends of the intubation assistance instrument 11, respectively, that is, the second internal bore 12B is formed into a through hole. By using such a second internal bore 12B, it is possible to aspirate substances inside the air passage, for instance, by means of a suction means such as a pump (not shown in the drawings) connected to the intubation assistance apparatus 100 in the assembled state.

The constituent material of the intubation assistance instrument 11 is not particularly limited, but various polymer materials such as polycarbonate and the like are preferably used.

As shown in FIG. 1, the main body 10 includes a grip section 103, a display 20, a coupling portion 104 for coupling the grip section 103 to the display 20, and a coupling member 101.

The grip section 103 is a portion of the intubation assistance apparatus 100 which is to be grasped by an operator with his one or both hands when the intubation assistance apparatus 100 in the assembled state is actually used (see FIG. 3). Note that FIG. 3 shows a state that the grip section 103 is grasped by an operator with his one hand.

The outer profile of the grip section 103 has a roughly column-like shape. Due to this shape, it is possible to grasp the grip section 103 easily and reliably, whereby enabling the intubation assistance instrument 11 to be inserted into the trachea of a patient easily and reliably by manipulating the intubation assistance apparatus 100 in the assembled state.

On the distal end portion of the grip section 103, the coupling member 101 is mounted so that the coupling member 101 is rotatable about the central axis $O_2$ of the main body 10 (the grip section 103). The coupling member 101 is formed from an annular member.

Further, as described above, the female thread 102 is formed on the inner circumferential surface of the coupling member 101. As shown in FIG. 4, the female thread 102 is adapted to be threaded with the male thread formed on the proximal end portion of the intubation assistance instrument 11.

On the proximal end portion of the grip section 103, the coupling portion 104 is provided so as to extend from the grip section 103. The display 20 is provided on the coupling portion 104.

As shown in FIGS. 1 and 2, the display 20 is provided on the coupling portion 104, that is, on the proximal end portion of the main body 10.

The display 20 is formed into a plate-like shape having a rectangular outer peripheral shape, and includes a screen 21 for displaying an electronic image taken by the image taking means 70 in the assembled state of the intubation assistance apparatus 100.

The screen 21 is constructed from a liquid crystal device and an organic EL device or the like, and displays an image (electronic image) based on image light taken by the image taking means 70.

The display 20 is rotatably supported on the main body 10 through a rotational mechanism 30 so as to be rotatable with respect to the main body 10 along a plane extending from the side surface 105 of the main body 10.

Specifically, the display 20 is rotatable between a first position where the display 20 makes contact with the main body 10 (this position of the display 20 is shown by a solid line in FIGS. 1 and 2) and a second position where the display 20 is far away from the main body 10 (this position of the display 20 is shown in a two-dot chain line).

The rotational mechanism 30 may be constructed so that the display 20 is stopped at each of the first and second positions. Alternatively, the rotational mechanism 30 may be constructed so that the display 20 can be stopped at any desired position between the first and second positions in a nonstep manner, or so that the display 20 can be stopped at one of the predetermined positions (e.g. one of five steps) between the first and second positions in a stepwise manner.

As described above, since the display 20 is rotatable with respect to the main body 10, it is possible to direct the display 20 to a desired direction despite the direction of the intubation assistance instrument 11 in the assembled state of the intubation assistance apparatus 100. As a result, an operation for inserting the intubation assistance instrument 11 into a patient (hereinafter, this operation will be simply referred to as "insertion operation") can be carried out easily and reliably. Further, since the insertion operation can be carried out without bending the cervical region of a patient rearwardly, high safeness can be realized.

Further, normally, during the insertion operation of the intubation assistance instrument 11 into the trachea of a patient, the direction and posture of the intubation assistance instrument 11 is changed or rotated variously. According to the present embodiment, by rotating the display 20 to an appropriate angle during the insertion operation, it is possible to monitor the display 20 at an optimum angle.

Next, a description will be made with regard to the image taking means 70.

The image taking means 70 shown in FIG. 4 is provided to take an image of an observation site where the distal end of the intubation assistance instrument 11 is positioned as an electronic image. The image taking means 70 includes an image guide 13, an enlargement optical system 17, a CCD (image pick-up device), and a controller 18, and these components are arranged in this order along the longitudinal direction of the intubation assistance instrument 11.

In the assembled state, the image guide 13 is arranged inside the first internal bore 12A. As described above, the image guide 13 is composed from the bundle of optical fibers 13A and the objective lens 13B provided in front of the bundle of optical fibers 13A.

The image guide 13 takes reflected light (image light) reflected from the observation site where the distal end of the intubation assistance instrument 11 is positioned through the objective lens 13B, and the thus obtained image light (image of an object) is transmitted to the CCD through the bundle of optical fibers 13A. With this structure, when the air passage of the patient is secured by the intubation assistance instrument 11, it is possible to acquire image light (electronic image) of the rima glottidis or its vicinity (that is, a region from the larynx to the rima glottidis) of the patient. In this regard, it is to be noted that in the following description an image of the rima glottidis G displayed on the screen 21 of the display 20 will be referred to as "the rima glottidis image G1".

Namely, in this embodiment, the image guide 13 constitutes means for leading image light of an observation site (image of an object) to the image pick-up device.

The bundle of optical fibers 13A is constructed by bundling a number of optical fibers made of quartz, multi-component glass, plastics or the like.

The CCD 16 is provided inside the main body 10. In the main body 10, the CCD 16 is disposed at a position facing the proximal end of the image guide in the assembled state of the intubation assistance apparatus 100, and an image is formed thereon based on the image light acquired by means of the image guide 13. Namely, an image of the observation site where the distal end of the intubation assistance instrument 11 is positioned is formed by the CCD 16.

The enlargement optical system 17 is composed from magnifying lenses 17A and 17B and a diaphragm 17C, and the enlargement optical system 17 is arranged between the proximal end of the image guide 13 and the CCD 16. With this arrangement, an image based on the image light is formed on the CCD 16 with being enlarged. Note that the enlargement optical system that can be used in this embodiment is not limited to the optical system described above.

The controller 18 for displaying the electronic image on the display 20 (on the screen 21) is also provided inside the main body 10. The screen 21 of the display 20 displays the electronic image formed by the CCD 16 under the control of the controller 18.

Examples of the image that is to be displayed on the screen 21 of the display 20 include an image showing the rima glottidis of a patient in a state that the air passage of the patient is secured by the intubation assistance instrument 11.

Next, a description will be made with regard to an intubation tube 200 that is used in combination with the intubation assistance apparatus 100.

As shown in FIGS. 1 and 2, the intubation tube 200 is composed from a tube main body 201 and a connector 202 affixed to one end portion of the tube main body 201.

The tube main body 201 is made of an elastic material such as elastomer, rubber and the like. Further, the tube main body 201 has a substantially circular cross-section.

The connector 202 is used by being connected to a respirator when artificial respiration is carried out using the respirator. By using the intubation tube 200 having the above structure, it is possible to feed air into the trachea of a patient from the respirator with the state that the intubation tube 200 is being inserted into the trachea of the patient.

Now, as shown in FIG. 3, a target mark 80 is provided on the screen 21 of the display 20. The target mark 80 is a reference mark for adjusting or setting an advancing direction of the intubation tube 200 to the rima glottidis image G1 in the electronic image displayed on the screen.

The center 801 of the target mark 80 is placed at a point which is eccentrically shifted from the center C of the screen 21 (that is, the origin) in both the X-axis minus direction and the Y-axis plus direction.

For example, when the distal end of the intubation assistance instrument 11 of the intubation assistance apparatus 100 in the assembled state is positioned in the vicinity of the rima glottidis G1 of a patient as shown in FIG. 6, the intersection M of the central axis $O_1$ of the intubation assistance instrument 11 and the central axis $O_5$ of the field of view of the image taking means 70 (that is, the central axis $O_4$ of the first internal bore 12A) is located at a position slightly before the rima glottidis G (lower side in FIG. 6). In this state shown in FIG. 6, the center of the rima glottidis G2 is deviated from the central axis $O_5$ for the distance $L_1$. The eccentric distance $L_2$ of the center 801 of the target mark 80 in the X-axis minus direction is determined so as to correspond to the distance $L_1$.

By providing such a target mark 80 at that position, when the intubation tube 200 is pushed out from the distal end of the intubation assistance instrument 11 in a state that the target mark 80 is superimposed on the rima glottidis image G1 displayed on the screen 21 (FIG. 3 shows such a state), the distal end of the intubation tube 200 displayed as an electronic image in the electronic image displayed on the screen 21 is advanced toward the rima glottidis image G1. As a result, the intubation tube 200 pushed out from the distal end of the intubation assistance instrument 11 is properly advanced toward the rima glottidis G (see FIG. 6), and then inserted into the rima glottidis G reliably. Accordingly, the intubation assistance apparatus 100 can have superior manipulability in inserting the intubation tube 200 into the rima glottidis G of a patient.

As shown in FIG. 3, the target mark 80 is comprised of a plurality of line segments 802 which are arranged radially around the center 801 with the same spacing (in this embodiment, the target mark 80 is comprised of four line segments). In this embodiment, it should be noted that the ends of the line segments 802 directed to the center 801 do not extend to the center 801.

Further, the number of the line segments 802 is not limited to four, and it may be three or five or more.

Furthermore, the color of the target mark 80 is not limited to a specific color, but it is preferable that the color is any color other than red, and is more preferably green. By selecting such a color as a color of the target mark 80, it is possible to improve the visibility of the target marl 80 in a state that the intubation assistance apparatus 100 is actually used, that is, in a state that the screen 21 displays an image of the vicinity of the rima glottidis G which normally appears to be reddish. Therefore, by providing such a target mark 80 as described above, the intubation assistance apparatus 100 can have more superior manipulability in inserting the intubation tube 200 into the rima glottidis G of a patient.

Further, in the case where green which is a complementary color of red is selected as the color of the target mark 80, the operator of the intubation assistance apparatus 100 can visually recognize the target mark 80 even if the operator focus his attention to an image of the observation site displayed on the screen 21.

Furthermore, a method for forming the target mark 80 on the screen 21 is not limited to a specific method. For example, the target mark 80 may be formed on the screen 21 by printing. By using this method, it is possible to form the target mark 80 on the screen 21 easily. Alternatively, in the case where the screen 21 is a liquid crystal display and an image of an observation site is displayed on the liquid crystal display, the target mark 80 may be formed by superimposing it on the displayed electronic image.

Hereinbelow, a description will be made with regard to the steps for assembling the intubation assistance apparatus 100.

In assembling the intubation assistance apparatus 100, the proximal end of the image guide 13 (bundle of optical fibers 13A) is first connected to the main body 10.

Thereafter, the image guide 13 which has been connected to the main body 10 is inserted into the first internal bore 12A of the intubation assistance instrument 11.

Next, the male thread 111 of the intubation assistance instrument 11 is threaded with the female thread 102 of the main body 10. In this regard, it is to be noted that the method for coupling the intubation assistance instrument 11 to the main body 10 is not limited to the method mentioned above, and other various methods can be employed. Examples of such methods include a ratchet mechanism method, a bayonet mounting method, a cam method, a locking claw method and a magnetic method.

Further, as shown in FIGS. 1 and 2, in the assembled state of the intubation assistance apparatus 100, the distal end portion of the intubation assistance instrument 11 (that is, the distal end portion of the curved portion 11B) is directed to a direction which is substantially in parallel with a normal line of the screen 21 of the display 20.

With this structure, since the direction in which the observation site can be seen through the objective lens 13B is substantially in parallel with the direction through which the operator monitors the screen 21 of the display 20, the operator can manipulate the intubation assistance apparatus 100 based on the image displayed on the screen 21 of the display 20.

In the intubation assistance apparatus 100 assembled according the above steps, in the region of the curved portion 11B of the intubation assistance instrument 11, the central axis $O_3$ Of the groove 15 is substantially in parallel with the central axis $O_1$ of the intubation assistance instrument 11 as described above. Therefore, in the curved portion 11B, the central axis $O_6$ of the intubation tube 200 inserted into the groove 15 is also substantially in parallel with the central axis $O_1$ of the intubation assistance instrument 11 (see FIG. 6).

Further, as described above, the first internal bore 12A is positioned on the opposite side of the groove 15 with respect to the central axis $O_1$ of the intubation assistance instrument 11, and in the curved portion 11B, the central axis $O_4$ of the first internal bore 12A beyond the angled point 114 is inclined toward the groove 15 with respect to the central axis $O_1$ of the intubation assistance instrument 11. With this structure, in the intubation assistance apparatus 100 in the assembled state, the central axis $O_5$ which corresponds to the center of the field of view of the image taking means 70 is also positioned on the opposite side of the central axis $O_3$ Of the groove 15 (that is, the central axis $O_6$ of the intubation tube 200 held by the groove 15) with respect to the central axis $O_1$ of the intubation assistance instrument 11 and also inclined toward the groove 15 with respect to the central axis $O_1$ of the intubation assistance instrument 11 (see, for example, FIG. 6).

Next, a description will be made with regard to one exemplary use (operation) of the intubation assistance apparatus 100 in the assembled state.

The intubation assistance apparatus 100 is used in such an instance that a patient has lost consciousness and a need exists to insert the intubation tube 200 into the trachea of the patient.

[1] First, the intubation assistance apparatus 100 is assembled in preparation for insertion of the intubation tube 200, and then confirmation is made as to whether or not the LED for illumination (not shown in the drawings) and the liquid crystal image are properly operated.

[2] Next, the intubation assistance instrument 11 of the intubation assistance instrument 100 is inserted (pushed) into the rima glottidis G of the patient through the mouth of the patient. More specifically, the intubation assistance instrument 11 is inserted into the mouth of the patient, while allowing the inner side of the curved portion 11B of the intubation assistance instrument 11 to extend along the root of the tongue. As a result, an appropriate area on the distal end side of the intubation assistance instrument 11 is brought into contact with the tongue root portion of the patient, thus securing an air passage of the patient. At this time, the intubation assistance instrument 11 is in a state shown in FIG. 6. Namely, the distal end of the intubation assistance instrument 11 is located at a position slightly before the rima glottidis G and the intersection M of the central axis $O_1$ of the intubation assistance instrument 11 and the central axis $O_5$ of the field of view of the image taking means 70 is also located at a position slightly before the rima glottidis G.

Further, when inserting the intubation assistance instrument 11 into the mouth of the patient, the operator can manipulate the intubation assistance instrument 11 with monitoring the screen 21 of the display 20. This makes it possible for the operator to manipulate the intubation assistance instrument 11 accurately so that the distal end of the intubation assistance instrument 11 is advanced toward the rima glottidis G of the patient.

Furthermore, as described above, in the intubation assistance instrument 100 of the present invention, the display 20 is provided on the main body 10 in a rotatable manner. Although the direction and posture of the intubation assistance instrument 11 is changed or rotated variously during the insertion operation of the intubation assistance instrument 11 into the rima glottidis G or its vicinity of the patient, it is possible to monitor the screen 20 of the display 20 at an optimum angle by rotating the display 20 to an appropriate angle during the insertion operation.

[3] Once the air passage is secured by the distal end of the intubation assistance instrument 11, an image of the rima glottidis and its vicinity of the patient (that is, the observation site) is taken.

[4] Then, data of the image of the object obtained in the previous step is sent to the display 20 through the controller 18, and an electronic image of the rima glottidis and its vicinity of the patient is displayed on the screen 21 of the display 20.

[5] Then, the intubation assistance apparatus 100 is manipulated so that it becomes a state shown in FIG. 6, that is, the intubation assistance apparatus 100 is manipulated so that the target mark 80 is superimposed on the rima glottidis image G1 displayed on the screen 21. As a result, the rima glottidis G is positioned on the extended line of the central axis $O_6$ of the intubation tube 200 held by the groove 15 (see FIG. 6).

[6] Then, the intubation tube 200 is inserted into the groove 15 from the proximal end portion of the intubation assistance instrument 11 with maintaining the state described above [5]. The intubation tube 200 inserted in the groove 15 is pushed forward, so that the intubation tube 200 is slidably moved forward within the groove 15. By further pushing the intubation tube 200 forward, the intubation tube 200 reaches at the distal end of the groove 15 while being bent in the curved portion 11B, and then the intubation tube 200 protrudes from the distal end of the intubation assistance instrument 11. At this time, an electronic image of the intubation tube 200 protruding from the distal end of the intubation assistance instrument 11 appears in the image displayed on the screen 21, and the situation that the intubation tube 200 is advancing toward the rima glottidis image G1 can be observed.

Thereafter, the intubation tube 200 reaches at the rima glottidis G. Then, by further advancing the intubation tube 200, the intubation tube 200 is inserted into the trachea of the patient through the rima glottidis G.

As described above, in the intubation assistance apparatus 100, in the region of the curved portion 11B of the intubation assistance instrument 11, the central axis $O_6$ of the intubation tube 200 held within the groove 15 is substantially in parallel with the central axis $O_1$ of the intubation assistance instrument 11 as described above, and the central axis $O_5$ which corresponds to the center of the field of view of the image taking means 70 is also positioned on the opposite side of the groove 15 with respect to the central axis $O_1$ of the intubation assistance instrument 11 and also inclined toward the groove 15 with respect to the central axis $O_1$ of the intubation assistance instrument 11. Due to the arrangement among these central axes described above, the center of the target mark 80 is placed at a position eccentric from the center C of the screen 21.

With this structure, the target mark 80 can be superimposed on the rima glottidis image G1 displayed on the screen 21 so that the rima glottidis G is positioned in front of the advancing direction of the intubation tube 200 protruding from the distal end of the intubation assistance instrument 11. As a result, the intubation tube 200 can be intubated into the trachea of a patient through the rima glottidis G thereof reliably in a short time. That is, the intubation assistance apparatus 100 can have more superior manipulability in the intubation operation of the intubation tube 200.

[7] Under the state that the intubation tube 200 remains inserted into the trachea, the intubation tube 200 is deformed and detached from the groove 15. While maintaining this condition, the intubation assistance instrument 11 is removed or taken out from the mouth of the patient so that only the intubation tube 200 remains being inserted into the mouth of the patient.

In the manner as described above, the intubation tube 200 can be intubated into the trachea of the patient.

In this regard, it is to be noted that in general the proximal end of the intubation tube 200 is connected to an artificial respirator, and air is fed into the trachea of a patient from the respirator through the intubation tube 200 which is inserted into the trachea of the patient through the rima glottidis thereof.

While the intubation assistance apparatus of the present invention has been described hereinabove in respect of the illustrated embodiment, this is not intended to limit the scope of the present invention. Instead, each component or element of the intubation assistance apparatus may be replaced with other one that exhibits the same or similar function. Furthermore, other arbitrary components than disclosed above may be added thereto.

For example, in the above embodiment, although the display is rotatably provided on the main body, the display may be fixedly mounted on the main body.

Further, in the above embodiment, although the target mark is placed at a position eccentrically shifted from the center of the screen in both the X-axis minus direction and the Y-axis plus direction, the target mark 80 may be placed at a position eccentrically shifted from the center of the screen only in either of the X-axis plus direction or the X-axis minus direction or either of Y-axis plus direction or Y-axis minus direction.

Furthermore, the target mark is not limited to one which is formed from a plurality of line segments. However, the target mark may be formed into a circular shape, a square shape, a rhomboid shape, a triangle shape, and a shape formed of a number of dots, and any arbitral combination of two ore more of these shapes.

Moreover, the method for forming the target mark on the screen is not limited to the printing method mentioned above, and the target mark may be formed by other methods such as a method for forming the target mark on the screen by carving, a method for sticking the target mark on the screen, and a method for forming the target marl as an electronic image, and the like.

Finally, it is also to be understood that the present disclosure relates to the subject matter contained in Japanese Patent Application No. 2005-309153 filed on Oct. 24, 2005 which is expressly incorporated herein by reference in its entirety.

What is claimed is:

1. An intubation assistance apparatus adapted for inserting an intubation tube into a target site of a patient, comprising:
    a main body having a distal end portion and a proximal end portion opposite to the distal end portion;
    an intubation assistance instrument provided on the distal end portion of the main body, the intubation assistance instrument having an elongated insertion section for insertion near the target site of the patient from the mouth of the patient, the insertion section having a central axis, the insertion section being formed with guide means for leading the intubation tube toward the target site when the intubation tube is to be inserted into the target site of the patient, the guide means being provided along a longitudinal direction of the insertion section and having a central axis generally parallel with the central axis of the insertion section;
    image taking means for taking an image of an observation site at a distal end portion of the insertion section as an electronic image, the image taking means being located on an opposite side of the guide means with respect to the central axis of the insertion section;
    a display provided on the proximal end portion of the main body and having a screen;
    a controller provided inside the main body, the controller controlling the display so as to display electronic images, including the electronic image taken by the image taking means, on the screen; and
    a target mark fixedly provided on the screen for indicating an advancing direction of the intubation tube, the target mark being different from any electronic image displayed on the screen, and the target mark being indicated at a position in which a center of the target mark is eccentrically shifted from a center of the screen so as to be located on a same side of the guide means with respect to the central axis of the insertion section.

2. The intubation assistance apparatus as claimed in claim 1, wherein the intubation assistance apparatus is configured so that the intubation tube is advanced toward the target site in the electronic image displayed on the screen when the intubation tube is pushed out from the distal end of the insertion section with a state that the target mark is set to the target site in the electronic image displayed on the screen.

3. The intubation assistance apparatus as claimed in claim 2,
    wherein a central axis of a field of view of the image taking means is inclined with respect to the central axis of the insertion section so as to be directed toward the intubation tube inserted into the guide means.

4. The intubation assistance apparatus as claimed in claim 3, wherein the target site is positioned on an extended line of a central axis of the intubation tube held by the guide means in a state that the target mark is set to the target site in the electronic image displayed on the screen.

5. The intubation assistance apparatus as claimed in claim 1, wherein the color of the target mark is any color other than red.

6. The intubation assistance apparatus as claimed in claim 1, wherein the color of the target mark is green.

7. The intubation assistance apparatus as claimed in claim 1, wherein the target mark is fixedly provided on the screen by printing it on the screen.

8. The intubation assistance apparatus as claimed in claim 1, wherein the main body has a proximal end surface,
   wherein the display has a rectangular shape and a rotation axis extending along a short side thereof, and is rotatably provided on the proximal end surface of the main body through the rotation axis,
   wherein the display is capable of moving between a first position where the display is close to the main body and a second position where the display is far away from the main body, and
   wherein the display has an outer peripheral shape corresponding to a shape of the proximal end surface of the main body and a planar size smaller than that of the proximal end surface of the main body.

9. The intubation assistance apparatus as claimed in claim 1, wherein the guide means is configured so that the intubation tube can be removed from the guide means in a state that the insertion section is inserted near the target site of the patient.

10. The intubation assistance apparatus as claimed in claim 1, wherein the image taking means includes an image pick-up device provided in the main body and leading means provided in the intubation assistance instrument for leading an image of an objection to be taken to the image pick-up device.

11. An intubation assistance apparatus adapted for inserting an intubation tube into a target site of a patient, comprising:
   a main body having a distal end portion and a proximal end portion opposite to the distal end portion;
   an intubation assistance instrument provided on the distal end portion of the main body, the intubation assistance instrument having an elongated insertion section for insertion near the target site of the patient from the mouth of the patient, the insertion section having a central axis, the insertion section being formed with a guide for leading the intubation tube toward the target site when the intubation tube is to be inserted into the target site of the patient, the guide being provided along a longitudinal direction of the insertion section and having a central axis generally parallel with the central axis of the insertion section;
   an imager configured to take an image of an observation site at a distal end portion of the insertion section as an electronic image, the imager being located on an opposite side of the guide with respect to the central axis of the insertion section;
   a display provided on the proximal end portion of the main body and having a screen;
   a controller provided inside the main body, the controller controlling the display so as to display electronic images, including the electronic image taken by the image taking means, on the screen; and
   a target mark fixedly provided on the screen for indicating an advancing direction of the intubation tube, the target mark being different from any electronic image displayed on the screen, and the target mark being indicated at a position in which a center of the target mark is eccentrically shifted from a center of the screen so as to be located on a same side of the guide with respect to the central axis of the insertion section.

12. The intubation assistance apparatus as claimed in claim 11, wherein the intubation assistance apparatus is configured so that the intubation tube is advanced toward the target site in the electronic image displayed on the screen when the intubation tube is pushed out from the distal end of the insertion section with a state that the target mark is set to the target site in the electronic image displayed on the screen.

13. The intubation assistance apparatus as claimed in claim 12,
   wherein a central axis of a field of view of the imager is inclined with respect to the central axis of the insertion section so as to be directed toward the intubation tube inserted into the guide.

14. The intubation assistance apparatus as claimed in claim 13, wherein the target site is positioned on an extended line of a central axis of the intubation tube held by the guide in a state that the target mark is set to the target site in the electronic image displayed on the screen.

15. The intubation assistance apparatus as claimed in claim 11, wherein the color of the target mark is any color other than red.

16. The intubation assistance apparatus as claimed in claim 11, wherein the color of the target mark is green.

17. The intubation assistance apparatus as claimed in claim 11, wherein the target mark is fixedly provided on the screen by printing it on the screen.

18. The intubation assistance apparatus as claimed in claim 11, wherein the main body has a proximal end surface,
   wherein the display has a rectangular shape and a rotation axis extending along a short side thereof, and is rotatably provided on the proximal end surface of the main body through the rotation axis,
   wherein the display is capable of moving between a first position where the display is close to the main body and a second position where the display is far away from the main body, and
   wherein the display has an outer peripheral shape corresponding to a shape of the proximal end surface of the main body and a planar size smaller than that of the proximal end surface of the main body.

19. The intubation assistance apparatus as claimed in claim 11, wherein the guide is configured so that the intubation tube can be removed from the guide in a state that the insertion section is inserted into the observation site of the patient.

20. The intubation assistance apparatus as claimed in claim 11, wherein the imager includes an image pick-up device provided in the main body and a leader provided in the intubation assistance instrument for leading an image of an objection to be taken to the image pick-up device.

* * * * *